US008786946B2

(12) United States Patent  (10) Patent No.: US 8,786,946 B2
 Nakamura  (45) Date of Patent: Jul. 22, 2014

(54) SURGICAL MICROSCOPE SYSTEM

(75) Inventor: Katsushige Nakamura, Chofu (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 746 days.

(21) Appl. No.: 12/306,119

(22) PCT Filed: Jun. 27, 2007

(86) PCT No.: PCT/JP2007/062939

§ 371 (c)(1),
(2), (4) Date: Dec. 22, 2008

(87) PCT Pub. No.: WO2008/001822

PCT Pub. Date: Jan. 3, 2008

(65) Prior Publication Data

US 2009/0190209 A1    Jul. 30, 2009

(30) Foreign Application Priority Data

Jun. 29, 2006  (JP) .................................. 2006-179986

(51) Int. Cl.
 *G02B 21/00*  (2006.01)
 *G02B 21/22*  (2006.01)
 *G02B 21/36*  (2006.01)

(52) U.S. Cl.
 CPC .............. *G02B 21/22* (2013.01); *G02B 21/361* (2013.01); *G02B 21/0012* (2013.01)
 USPC ............ 359/378; 359/363; 359/368; 359/369

(58) Field of Classification Search
 CPC ... G02B 21/0012; G02B 21/22; G02B 21/361
 USPC .................... 359/368–390, 462–467
 See application file for complete search history.

(56) References Cited

U.S. PATENT DOCUMENTS 4,786,154 A * 11/1988 Fantone et al. ............... 359/369
5,067,804 A * 11/1991 Kitajima et al. .............. 359/369

(Continued)

FOREIGN PATENT DOCUMENTS

EP  1333305  8/2003
JP  2607828 B2  2/1997

(Continued)

OTHER PUBLICATIONS

English language Abstract of JP 2005-137932 A (Jun. 2, 2005).

(Continued)

*Primary Examiner* — Thong Nguyen
(74) *Attorney, Agent, or Firm* — Greenblum & Bernstein, P.L.C.

(57) ABSTRACT

The surgical microscope system includes a first binocular microscope and a first display device. The first binocular microscope includes an objective lens, a first right ocular lens which provides a first image based on a light flux transmitted through the objective lens, and a first left ocular lens which provides a second image based on a light flux transmitted through the objective lens. The first display device can be disposed opposite to or in alignment with the first binocular microscope, and includes a first right-eye image display surface for displaying the first image and a first left-eye image display surface for displaying the second image. The first display device can be reversed about a horizontal axis extending in a direction along which the first right-eye image display surface and the first left-eye image display surface are located in alignment.

10 Claims, 15 Drawing Sheets

(56) References Cited

U.S. PATENT DOCUMENTS

| | | | |
|---|---|---|---|
| 5,825,532 A | | 10/1998 | Mochizuki et al. |
| 5,867,210 A | * | 2/1999 | Rod ............................ 348/51 |
| 6,525,878 B1 | | 2/2003 | Takahashi |
| 7,002,738 B2 | * | 2/2006 | Sturgis et al. ................ 359/384 |
| 7,180,660 B2 | | 2/2007 | Hauger et al. |
| 7,190,513 B2 | * | 3/2007 | Obrebski et al. ............. 359/376 |
| 7,480,093 B2 | * | 1/2009 | Sander .......................... 359/369 |
| 7,512,437 B2 | * | 3/2009 | Banju et al. .................. 600/476 |
| 8,115,993 B2 | | 2/2012 | Hauger et al. |
| 8,144,393 B2 | * | 3/2012 | Nakamura ................... 359/376 |
| 2003/0112509 A1 | | 6/2003 | Takahashi |
| 2004/0017607 A1 | | 1/2004 | Hauger et al. |
| 2004/0036962 A1 | * | 2/2004 | Brunner et al. .............. 359/368 |
| 2007/0127115 A1 | | 6/2007 | Hauger et al. |
| 2010/0238541 A1 | | 9/2010 | Hauger et al. |

FOREIGN PATENT DOCUMENTS

| | | |
|---|---|---|
| JP | 2001-117049 A | 4/2001 |
| JP | 2001-145640 | 5/2001 |
| JP | 2004-347690 A | 12/2004 |
| JP | 2005-137577 A | 6/2005 |
| JP | 2005-137932 A | 6/2005 |

OTHER PUBLICATIONS

English language Abstract of JP 7-104193 A (Apr. 21, 1995).
English language Abstract of JP 2001-117049 A (Apr. 27, 2001).
English language Abstract of JP 2005-137577 A (Jun. 2, 2005).
English language Abstract of JP 2004-347690 A (Dec. 9, 2004).
Extended European Search Report (EESR) from European Patent Office (EPO) in European Patent Application No. 07767737.5, dated Feb. 26, 2014.

* cited by examiner

SURGICAL MICROSCOPE SYSTEM

TECHNICAL FIELD

The present invention relates to a surgical microscope system which provides magnified images of the operation site, and particularly to a surgical microscope system which can provide magnified images to the principal operator and an assistant operator of the surgery.

BACKGROUND ART

In recent years, along with development of medical technology, microsurgery using a surgical microscope has been widely performed. In microsurgery, there may be a case where an assistant operator who assists the principal operator is needed in addition to the principal operator (surgeon), particularly for a complex surgery. In this case, not only the principal operator but also the assistant operator may need to observe the operation site in a magnified manner, for which a surgical microscope has been developed as disclosed in Japanese Unexamined Patent No. 2005-137932 wherein a microscope is also disposed for use by the assistant operator in addition to the microscope for use by the principal operator.

As such a microscope for use by the assistant operator, a side-view microscope is disposed at the side of the microscope (main microscope) for use by the principal operator. When the main microscope is moved by the principal operator in order to shift the observation position during the surgery, the side-view microscope is also moved because the side-view microscope is disposed to the main microscope itself. There has been an inconvenience that the assistant operator must also move accordingly.

Additionally, in order to solve the above problem, as disclosed in Japanese patent No. 2607828, a surgical microscope has been developed, comprising a video microscope which captures images of the operation site using a camera instead of the side-view microscope and displays its stereoscopic images on a small size liquid crystal display (LCD). With the surgical microscope, the above-mentioned inconvenience is solved because the video microscope can be provided independently from the main microscope. In addition, the assistant operator can observe the operation site not only from a side position of the principal operator but also from an opposite position, when the small-size LCD is moved.

However, with the main microscope disclosed in Japanese patent No. 2607828, the image observed by the assistant operator through the small-size LCD is a visual field image observed by the principal operator at his/her view point. Accordingly, there is an inconvenience that the assistant operator may be confused in grasping the sense of right-and-left or up-and-down relative to his/her standpoint. For example, if the assistant operator reaches out to the operation site when observing the operation site from a position opposite to the principal operator, the assistant operator sees his/her hand coming out from left upper side of his/her visual field. Or, if the assistant operator reaches out to the operation site when observing from a side position, he/she sees his/her hand coming out from the right side. In other words, since the assistant operator sees, through the small-size LCD, his/her hand moving in a direction different from the direction to which it is actually moving, there has been a problem that the assistant operator could not properly grasp the sense of distance, thereby preventing the assistant operator from properly assisting the principal operator.

SUMMARY OF THE INVENTION

It is an object of the present invention, which has been conceived to solve the above problems, to provide a surgical microscope system which allows an assistant operator to observe the operation site in a magnified manner within his/her own visual field from a position in alignment with, or from a position opposite to, or at a right-front or left-front position of the principal operator.

In order to solve the above problems, a first aspect of the present invention provides a surgical microscope system comprising: a first binocular microscope that includes an objective lens, a first right ocular lens which provides a first image based on a light flux transmitted through the objective lens, and a first left ocular lens which provides a second image based on a light flux transmitted through the objective lens; and a first display device that can be disposed opposite to or in alignment with the first binocular microscope, includes a first right-eye image display surface for displaying the first image and a first left-eye image display surface for displaying the second image, and can be reversed about a horizontal axis extending in a direction along which the first right-eye image display surface and the first left-eye image display surface are located in alignment.

Here, disposing at an opposite position refers to locating the first display device relative to the first binocular microscope so that the assistant operator assisting the principal operator can assist the surgery while facing the principal operator with the operation site being located between them. However, "facing" in this case does not necessarily mean that the angle between the principal operator and the assistant operator is strictly 180° across the operation site, but may be slightly off 180°, provided that the assistant operator can properly assist the surgery.

In addition, the horizontal axis is not necessarily required to be strictly "horizontal", but should be understood that it is sufficiently horizontal to an extent such that the principal operator or the assistant operator can look into the display device without difficulty after having rotated the display device.

A second aspect of the present invention provides a surgical microscope system according to the surgical microscope system of the first aspect, further comprising a first branching device and a second branching device that bifurcate a light flux transmitted through the objective lens, wherein the first image is provided by the first right ocular lens using one of light fluxes bifurcated by the first branching device, and the first image is displayed on the first right-eye image display surface based on the other one of the light fluxes, and the second image is provided by the first left ocular lens using one of light fluxes bifurcated by a second branching device, and the second image is displayed on the first left-eye image display surface based on the other one of the light fluxes.

A third aspect of the present invention provides a surgical microscope system according to the surgical microscope system of the second aspect, wherein the first display device further comprises a first imaging device into which the other one of the light fluxes bifurcated by the first branching device and the other one of the light fluxes bifurcated by the second branching device are incident.

A fourth aspect of the present invention provides a surgical microscope system according to the surgical microscope system of the first aspect, further comprising a supporting stand, wherein the first binocular microscope and the first display device are attached to the supporting stand so that they can move independent of each other.

A fifth aspect of the present invention provides surgical microscope system comprising: a second binocular microscope that includes an objective lens, a second right ocular lens which provides a third image based on a light flux transmitted through the objective lens, and a second left ocular lens which provides a fourth image based on a light flux transmitted through the objective lens; and a second display device that includes a second right-eye image display surface for displaying a fifth image based on a light flux transmitted through the objective lens and a second left-eye image display surface for displaying a sixth image based on a light flux transmitted through the objective lens.

A sixth aspect of the present invention provides a surgical microscope system according to the surgical microscope system of the fifth aspect, wherein the third image is provided based on a first light flux transmitted through a first point of the objective lens, the fourth image is provided based on a second light flux transmitted through a second point which is symmetric with the first point about the optical axis of the objective lens, the fifth image is displayed based on a third light flux transmitted through a third point of the objective lens, and the sixth image is displayed based on a fourth light flux transmitted through a fourth point which is symmetric with the third point about the optical axis of the objective lens.

A seventh aspect of the present invention provides a surgical microscope system according to the surgical microscope system of the sixth aspect, wherein a line segment connecting the first point and the second point, and a line segment connecting the third point and the fourth point are perpendicular to each other.

An eighth aspect of the present invention provides a surgical microscope system according to the surgical microscope system of the sixth aspect, further comprising a second imaging device that receives an incident third light flux to generate the fifth image and to provide the fifth image to the second right-eye image display surface, and that receives an incident fourth light flux to generate the sixth image and to provide the sixth image to the second left-eye image display surface.

A ninth aspect of the present invention provides a surgical microscope system according to the surgical microscope system of the fifth aspect, wherein the second display device can be provided either at a right-front or left-front position of the second binocular microscope and can be reversed about a horizontal axis extending in a direction along which the second right-eye image display surface and the second left-eye image display surface are located in alignment.

Here, "right-front" or "left-front" refers to a position seen from the principal operator using the main microscope. Describing the positions in comparison to a clock face, when the principal operator is standing at the six o'clock position, right-front is a position approximately in the range of half past one to half past four, or three o'clock to be precise, whereas left-front a position approximately is in the range of half past seven to half past ten, or nine o'clock to be precise.

A tenth aspect of the of the present invention provides a surgical microscope system according to the surgical microscope system of the fifth aspect, further comprising a supporting stand, wherein the second binocular microscope and the second display device are attached to the supporting stand so that they can move independent of each other.

An eleventh aspect of the present invention provides a surgical microscope system according to the surgical microscope system of the fifth aspect, further comprising a third display device that is disposed opposite to the second display device and includes a third left-eye image display surface for displaying the fifth image in an upside-down manner and a third right-eye image display surface for displaying the sixth image in an upside-down manner.

A twelfth aspect of the present invention provides a surgical microscope system according to the surgical microscope system of the fifth aspect, further comprising a fourth display device that can be disposed opposite to or in alignment with the second binocular microscope, includes a fourth right-eye image display surface for displaying the third image and a fourth left-eye image display surface for displaying the fourth image, and can be reversed about a horizontal axis extending in a direction along which the fourth right-eye image display surface and the fourth left-eye image display surface are located in alignment.

A thirteenth aspect of the present invention provides a surgical microscope system according to the surgical microscope system of the twelfth aspect, further comprising a third imaging device that receives an incident first light flux to generate the third image and provide the third image to the fourth right-eye image display surface, and that receives an incident second light flux to generate the fourth image and to provide the fourth image to the fourth left-eye image display surface.

A fourteenth aspect of the present invention provides a surgical microscope system according to the surgical microscope system of the fifth aspect, further comprising a fifth display device that is disposed opposite to the second display device and includes a fifth left-eye image display surface for displaying the third image in an upside-down manner and a fifth right-eye image display surface for displaying the fourth image in an upside-down manner.

According to the present invention, a surgical microscope system is provided which allows an assistant operator to observe the operation site in a magnified manner within his/her own visual field from a position in alignment with, or opposite to, or the right-front or left-front of, the principal operator.

BEST MODES FOR CARRYING OUT THE INVENTION

Figure 1:
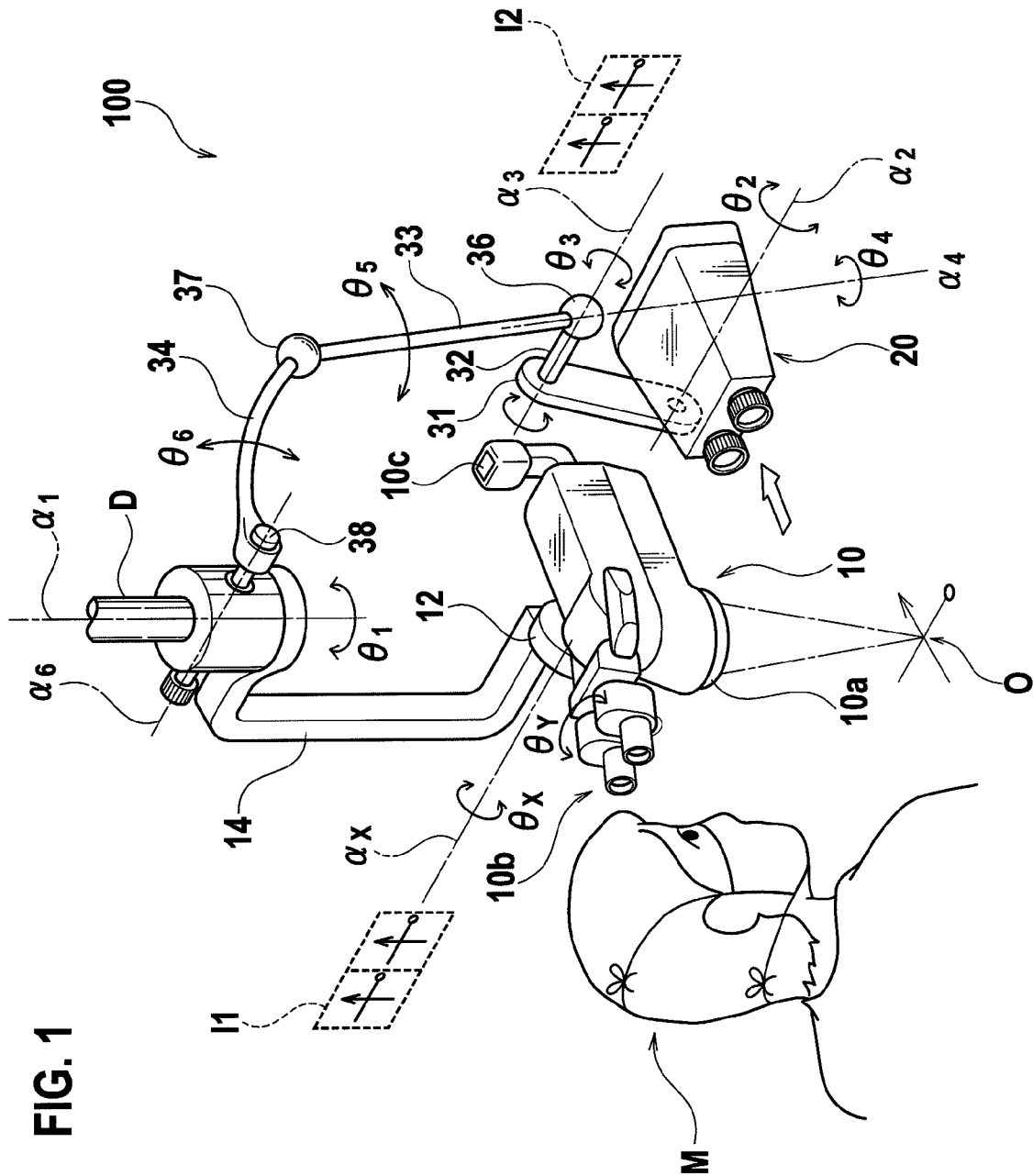
FIG. 1 is a perspective view illustrating a surgical microscope system according to a first embodiment of the present invention, in which a stereo viewer is disposed in alignment with the main microscope.

The surgical microscope system according to embodiments of the present invention will be described below, referring to the accompanying drawings. Here, like elements in the drawings are provided with like reference numerals, and duplicate description is omitted. In addition, the accompanying drawings illustrate the surgical microscope of respective embodiments only schematically. Therefore it should be noticed that proportions between respective components are not necessarily expressed faithful to the actual design.

First Embodiment

Referring to FIG. 1, the surgical microscope system 100 comprises a medical optical instrument stand (not shown), a main microscope 10 attached to a tip arm D of the medical optical instrument stand via a predefined arm (described below), and a stereo viewer 20.

The main microscope 10 is mainly used by the principal operator M (surgeon) to magnify the operation site O for observation. As shown, the main microscope 10 is attached to one end of an arm 14 via an electro-magnetic clutch 12. As well as allowing the main microscope 10 to rotate in the $\theta_X$ direction about the axis $\alpha_X$, the electro-magnetic clutch 12 can fix the main microscope 10 at a predefined angle. The other end of the arm 14 is attached to the tip arm D of the medical optical instrument stand. The arm 14 is rotatable in the $\theta_1$ direction about the central axis $\alpha_1$ of the tip arm D. In addition, the main microscope 10 is also rotatable in the $\theta_Y$ direction by an electro-magnetic clutch which is not shown.

On the other hand, the stereo viewer 20 is attached to the tip arm D by a support member including arms 31 to 34, the detail of which is as follows.

A stereo viewer 20 is attached to one end of the arm 31 and is rotatable in the $\theta_2$ direction about the axis $\alpha_2$ which is extending horizontally. The other end of the arm 31 is attached to one end of the arm 32 to be rotatable in the $\theta_3$ direction about the central axis $\alpha_1$ of the arm 32. Thus, the stereo viewer 20 can also rotate in the $\theta_3$ direction. The other end of the arm 32 is attached to one end of the arm 33 via a joint 36. The arm 32 is rotatable in the $\theta_4$ direction about the central axis $\theta_4$ of the arm 33 by the joint 36, and the stereo viewer 20 is also rotatable in the $\theta_4$ direction. The other end of the arm 33 is attached to one end of the arm 34 via a joint 37. The arm 33 is swingable by the joint 37 in the direction of $\theta_5$ in the figure, and the stereo viewer 20 is also swingable in the $\theta_5$ direction. The other end of the arm 34 is attached to the tip arm D of the medical optical instrument stand via a rod 38. The arm 34 is rotatable in the $\theta_6$ direction about the central axis $\alpha_6$ of the rod 38, and the stereo viewer 20 is also rotatable in the $\theta_6$ direction.

In addition, the stereo viewer 20 has built-in small-size LCDs 6 (6L and 6R) (FIG. 2) aligned along axis $\alpha_2$ to provide images displayed thereon to the user through a pair of finders 20 (20L and 20R). The images are provided from a pair of mirrors 2L and 2R included in the main microscope 10 and a television camera 10c, which will be described below.

Next, the optical structure of the main microscope 10 will be described.

Figure 2:
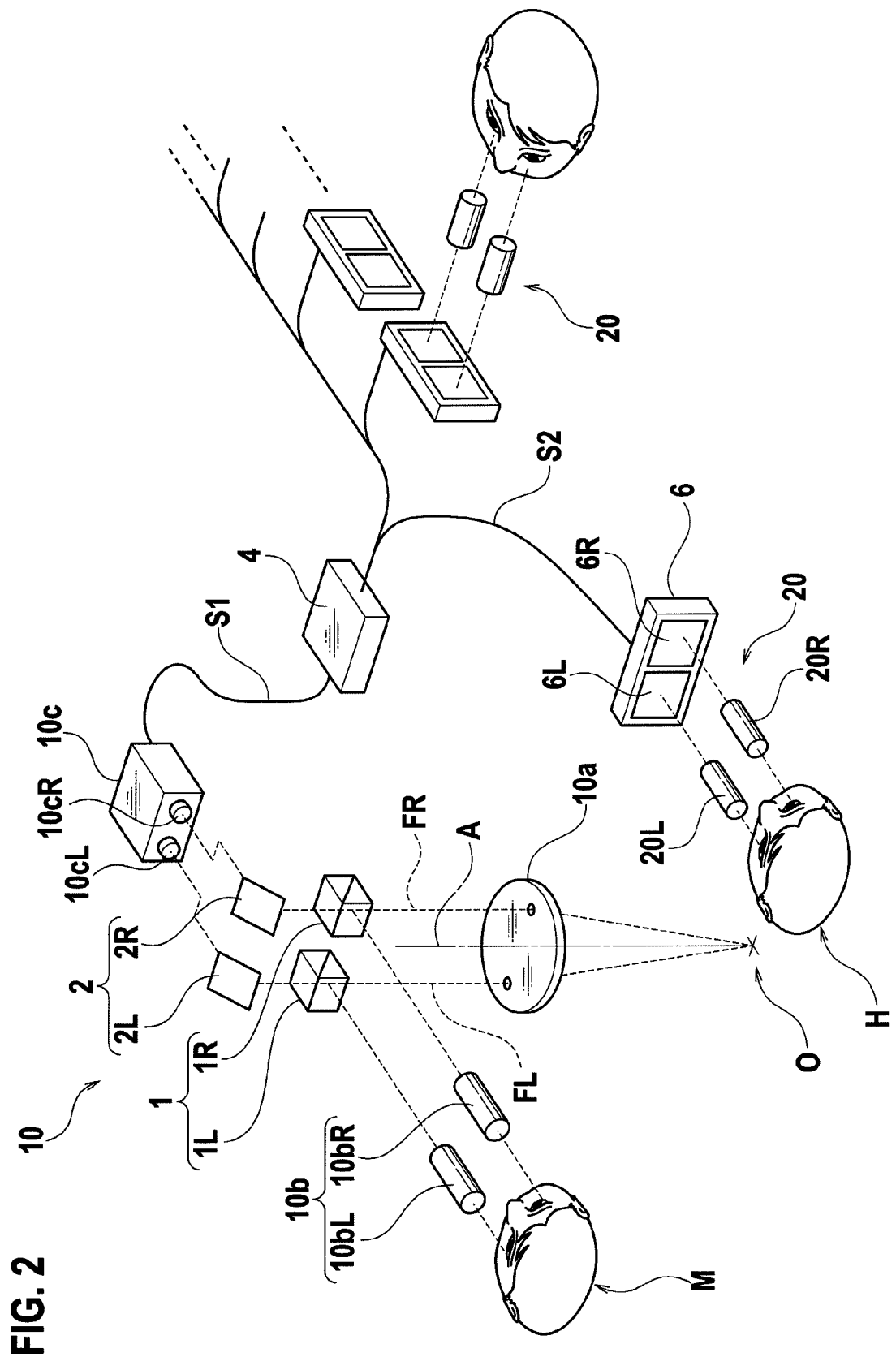
FIG. 2 is a schematic view illustrating the optical arrangement of the surgical microscope system shown in FIG. 1.

Referring to FIG. 2, the main microscope 10 includes an objective lens 10a, a pair of beam splitters 1 (1L and 1R), a pair of ocular lenses 10b (10bL and 10bR), the pair of mirrors 2 (2L and 2R), and the television camera 10c.

The objective lens 10a is disposed so that it faces toward the operation site O. This is realized by suitably using the medical optical instrument stand, the arm 14 and the electro-magnetic clutch 12 which have been mentioned above, and adjusting the position of the main microscope 10. In addition, the objective lens 10a is disposed to be vertically movable, with its focal point being manually or automatically adjustable. The beam splitters 1L and 1R are disposed symmetrically with each other about the optical axis A of the objective lens 10a above the objective lens 10a. The ocular lenses 10bL and 10bR are disposed so that they optically connect to the beam splitters 1L and 1R, respectively. The objective lens 10a, the beam splitters 1L and 1R, and the ocular lenses 10bL and 10bR are optically connected, specifically, in the following manner.

If the operation site O is illuminated by a predefined lighting device, the light reflected at the operation site O is incident into and transmits through the objective lens 10a. A portion (light flux FL) of the transmitted light is reflected by a beam splitter 1L, and is incident into the ocular lens 10bL. In addition, another portion (light flux FR) of the transmitted light is reflected by a beam splitter 1R, and is incident into the ocular lens 10bR. The light fluxes FL and FR which are incident into the ocular lenses 10bL and 10bR are magnified by the ocular lenses 10bL and 10bR, and a magnified image of the operation site O is provided to the principal operator M.

Here, according to the above-mentioned arrangement, the principal operator M sees a stereoscopic image because slightly different images of the operation site O are provided to the right and left eyes by a pair of beam splitters 1L and 1R disposed symmetrically with each other about the optical axis A. Therefore, the principal operator M can perceive the sense of depth (height), whereby it becomes easier to perform the surgery.

In addition, referring to FIG. 2, the mirrors 2L and 2R are disposed above the beam splitters 1L and 1R, respectively corresponding to them. The television camera 10c is disposed so that it is optically connected to the mirrors 2L and 2R. The television camera 10c, being a so-called stereo video camera (3-dimensional video camera), comprises two incidence lenses 10cL and 10cR (also referred to as television cameras 10cL and 10cR in the following), and generates an image based on the light flux which is incident into each of them.

The objective lens 10a, the beam splitters 1L and 1R, the mirrors 2L and 2R, and the television cameras 10cL and 10cR are optically connected, specifically in the following manner.

Since the beam splitters 1 are also transmissive, the above-mentioned light flux FL transmits through the beam splitter 1L. The light flux FL transmitted through the beam splitter 1L is reflected by the mirror 2L and enters the television camera 10cL. Similarly, the light flux FR is transmitted through the beam splitter 1R, reflected by the mirror 2R, and enters the television camera 10cR.

When the light fluxes FL and FR enter the television cameras 10cL and 10cR respectively, the light fluxes FL and FR are converted into electric signals by a photoelectric converter (not shown) provided in the television camera 10c, which the electric signals are transmitted to the image processor 4 through a signal line S1. Subsequently, the electric signals are transmitted to the small-size LCDs 6L and 6R through a signal line S2 from the image processor 4, where images based on the light fluxes FL and FR are displayed respectively.

Since the image displayed on the small-size LCD 6L and the image provided by the ocular lens 10bL are both based on the light flux FL, they are identical to each other. In addition, since the image displayed on the small-size LCD 6R and the image provided by the ocular lens 10bR are both based on the light flux FR, they are identical to each other. In this manner, a stereoscopic image provided by the main microscope 10 is duplicated and displayed by the stereo viewer 20.

Next, the major effect brought about by the surgical microscope system 100 according to the first embodiment will be described, referring to FIGS. 1, 3, and 4.

As stated above, since the stereo viewer 20 is movably attached to the tip arm D by the support member including the arms 31 to 34, the stereo viewer 20 can be disposed at a position opposite to the main microscope 10. In this case, the assistant operator H (FIG. 3) using the stereo viewer 20 can assist the surgery from a position facing the principal operator M who is using the main microscope 10.

Figure 3:
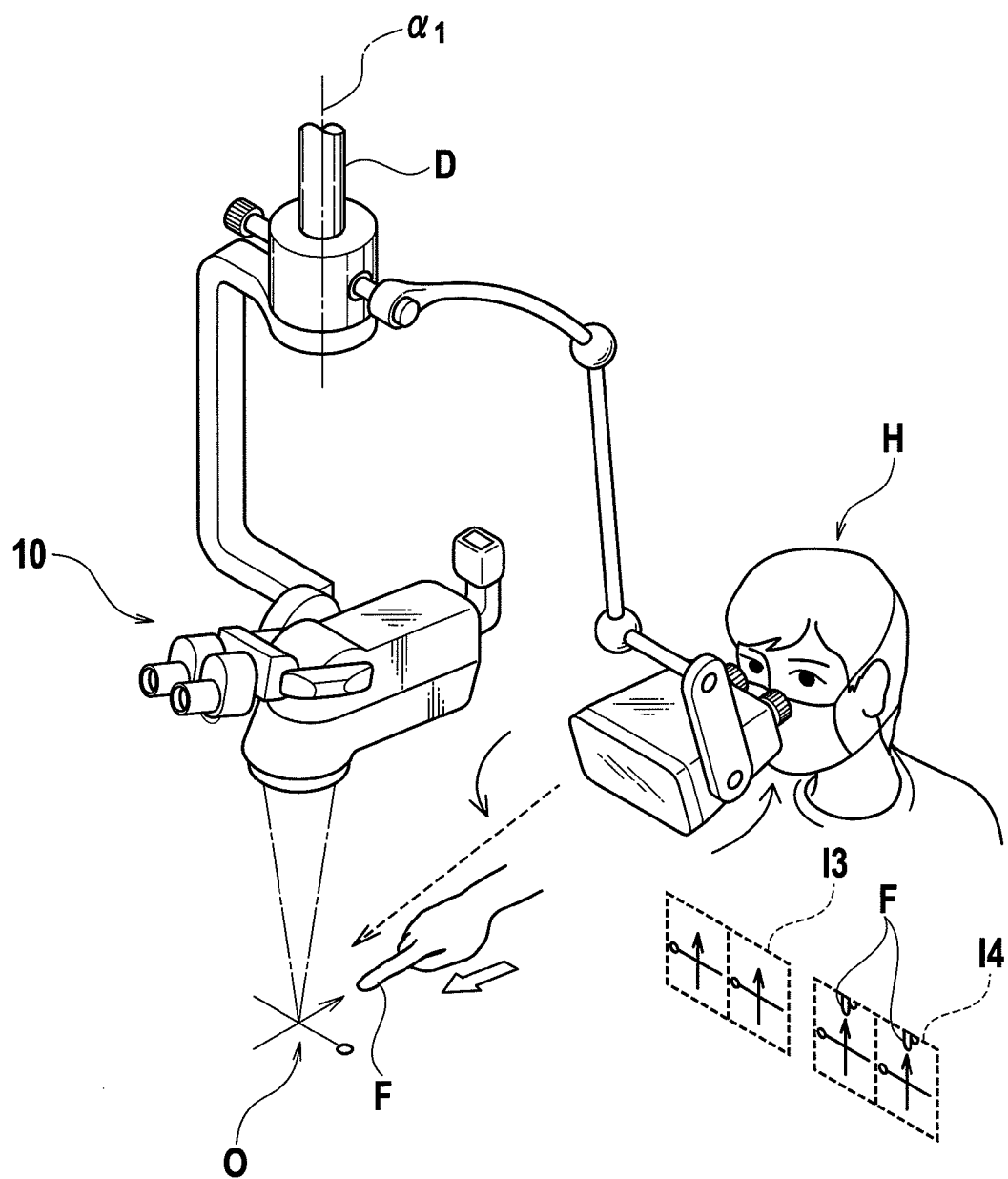
FIG. 3 is a schematic view illustrating a case where a stereo viewer is disposed opposite to the main microscope in the surgical microscope system according to the first embodiment of the present invention, presenting a comparative example to explain its effect.
Figure 4:
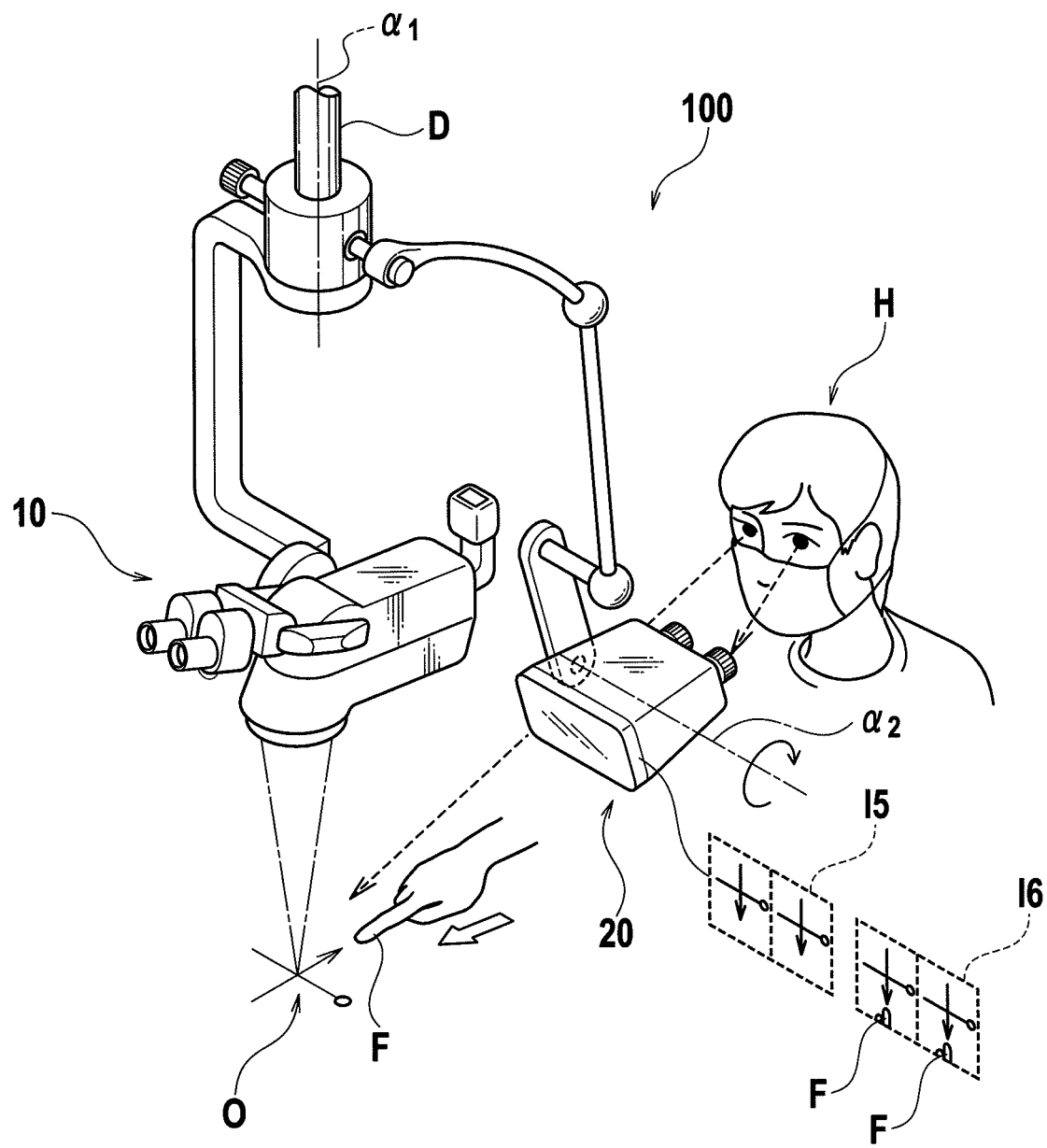
FIG. 4 is a schematic view illustrating a case where a stereo viewer is disposed opposite to the main microscope in the surgical microscope system according to the first embodiment of the present invention, in order to describe its effect in comparison with FIG. 3.

Here, for convenience of explanation, it is assumed that there is a figure shown in FIGS. 1, 3 and 4 (a figure of an intersecting arrow and a line segment, with a circle located at one end of the line segment) in the operation site O, with FIGS. 1, 3 and 4 schematically illustrating what kind of images (figures) the ocular lenses 10bL and 10bR and stereo viewer 20 of the main microscope 10 provide (see reference numerals I1 to I6).

When observing the operation site O through the main microscope 10, the principal operator M thus sees a figure including an upward arrow and a circle located at the right side (I1 of FIG. 1). In this occasion, since the stereo viewer 20 duplicates and displays the stereoscopic image provided from the main microscope 10 as mentioned above, it is likewise displaying a figure including an upward arrow and a circle located at the right side (I2 of FIG. 1).

Here, assuming that the stereo viewer 20 is moved to a position opposite to the main microscope 10 and rotated 180° horizontally about a predefined axis in the vertical direction, the stereo viewer 20 thus provides, as shown in FIG. 3, a figure including an upward arrow and a circle located at the right side, as with the main microscope 10, to the assistant operator H (I3). In this occasion, when the assistant operator H extends his/her finger F toward the operation site O, he/she sees his/her finger F extending from above in the image (I4). Accordingly, there has been an inconvenience that the assistant operator H may move his/her finger F away from the operation site O even if he/she must move his/her finger F close to the operation site O.

However, the stereo viewer 20 in the first embodiment can be reversed about the axis $\alpha_2$ as stated above. By such reversal, the image displayed by the stereo viewer 20 is also reversed, as shown in FIG. 4. Therefore, when the assistant operator H looks into the stereo viewer 20 after being reversed, he/she sees a figure consisting of a downward arrow with a circle located at the left side (I5). This corresponds to a magnified image of the operation site O observed from the position of the assistant operator H, whereby, the assistant operator H sees his/her finger F extending from below when the assistant operator H extends his/her finger F toward the operation site O (I6). Therefore, the assistant operator H can assist the surgery without losing sense of direction, or without being confused by the top-and-bottom or right-and-left relationship.

In addition, the surgical microscope system 100 has the following effects. Since the stereo viewer 20 is movably supported by the support member including the arms 31 to 34, the stereo viewer 20 can be disposed in alignment with the main microscope 10 (see FIG. 1). In this case, the assistant operator H using the stereo viewer 20 can use it while standing side-by-side with the principal operator M using the main microscope 10. Since the image provided by the stereo viewer 20 is identical to the image provided by the main microscope 10, the assistant operator H observes the operation site O from approximately his/her position in a magnified manner, and the assistant operator H can use it without losing sense of direction.

Furthermore, since the stereo viewer 20 is attached to the tip arm D of the medical optical instrument stand independent of the main microscope 10 as stated above, the stereo viewer 20 does not move following the main microscope 10 even if the principal operator M tilted the main microscope 10. Therefore, the surgical microscope system 100 according to the present embodiment is advantageous in that the assistant operator H can keep observing the operation site O without moving, even if the main microscope 10 is tilted.

Here, as shown in FIG. 2, when a plurality of stereo viewers 20 are connected to the image processor 4, images identical to the image provided by the main microscope 10 are displayed on the plurality of stereo viewers 20. Thus, a plurality of interns can observe a surgery performed by an experienced surgeon, for example. In other words, the surgical microscope system 100 according to the first embodiment is advantageous in that it contributes to enhancing the skill level of interns through the observation of the surgery performed by the experienced surgeon.

Second Embodiment

Figure 5:
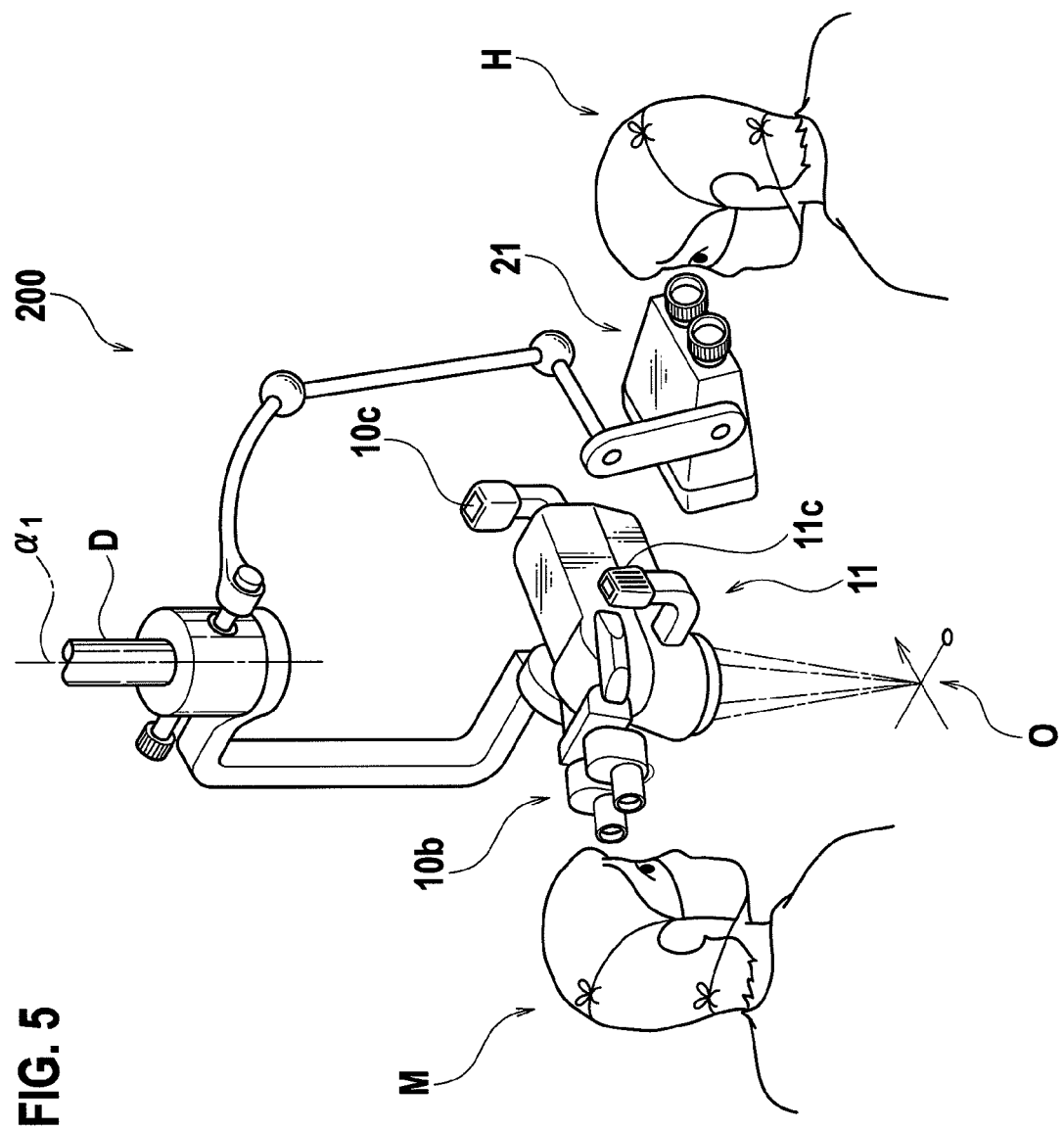
FIG. 5 is a perspective view illustrating a surgical microscope system according to a second embodiment of the present invention, and in which a stereo viewer is disposed at the right-front of the main microscope.

FIG. 5 is a schematic view illustrating a surgical microscope system according to a second embodiment. As shown, the surgical microscope system 200 comprises a main microscope 11 and a stereo viewer 21. The main microscope 11 is movably attached to the tip arm D of the medical optical instrument stand by a predefined arm, similarly with the main microscope 10 in the first embodiment. The main microscope 11 has an arrangement identical to that of the main microscope 10 in the first embodiment except that its internal optical structure is different, and it has an additional television camera 11c.

In addition, the stereo viewer 21 is movably attached to the tip arm D of the medical optical instrument stand by the support member including the arms 31 to 34, similarly with the stereo viewer 20 in the first embodiment. However, in the second embodiment, the stereo viewer 21 is disposed so that the assistant operator H using it can stand at the right front of the principal operator M using the main microscope 11, and face the operation site O from there. Except for this arrangement, the stereo viewer 21 has an identical arrangement as the stereo viewer 20 in the first embodiment.

Figure 6:
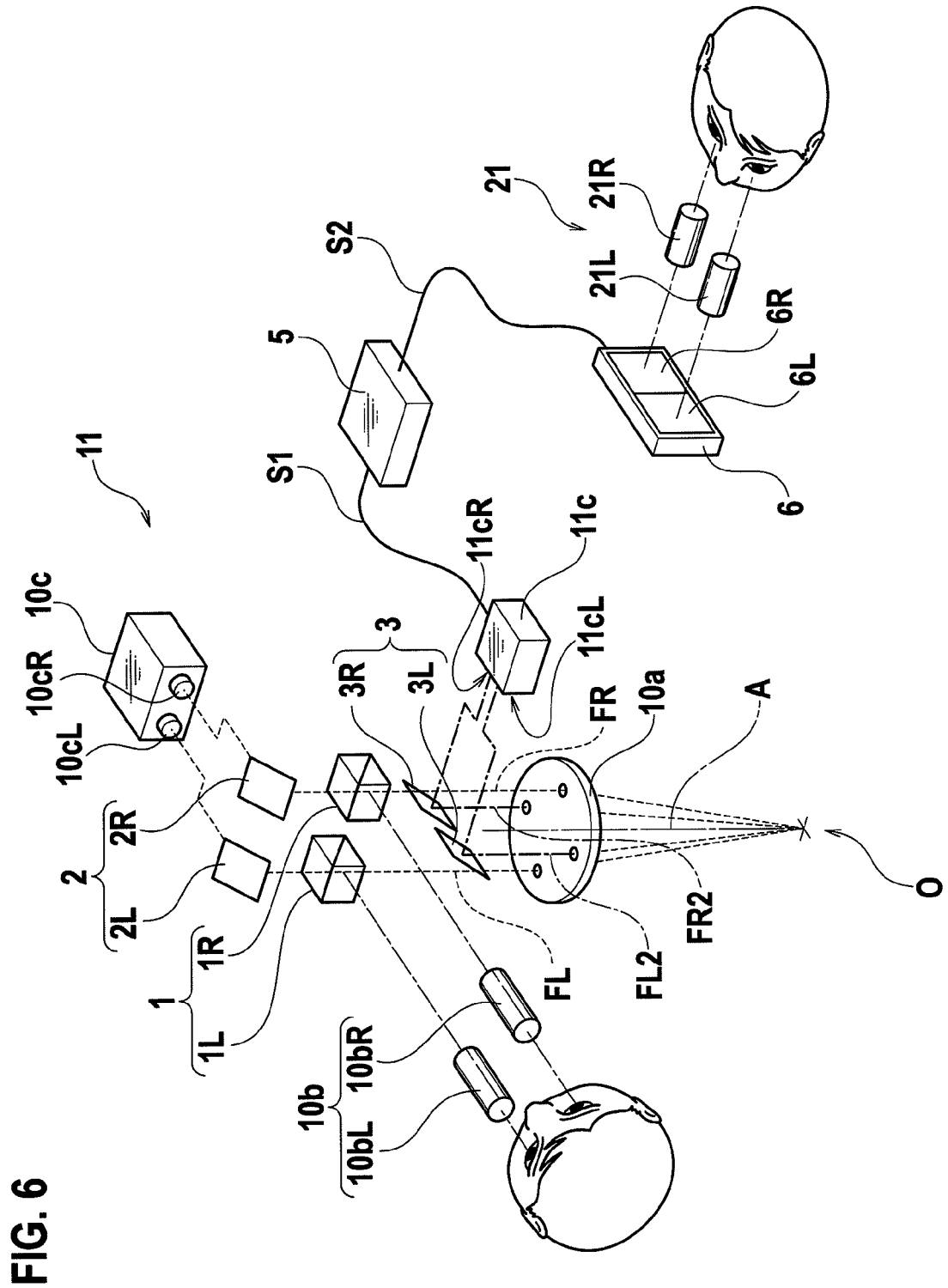
FIG. 6 is a schematic view illustrating the optical arrangement of the surgical microscope system according to the second embodiment of the present invention.

Referring to FIG. 6, the optical structure of the main microscope 11 will be described below. As shown, the main microscope 11 comprises, an objective lens 10a, beam splitters 1L and 1R, ocular lenses 10bL and 10bR, mirrors 2L and 2R, and a television camera 10c similarly as the main microscope 10 in the first embodiment, and additionally, comprises a pair of mirrors 3 (3L and 3R) and the television camera 11c.

The mirrors 3L and 3R are disposed above the objective lens 10a symmetrically to each other about the optical axis A. Particularly, the mirrors 3L and 3R are disposed so that an imaginary line connecting the mirrors 3L, 3R and an imaginary line connecting the beam splitters 1L and 1R are perpendicular to each other on the optical axis A.

In addition, the television camera 11c is disposed so that the mirrors 3L and 3R optically connect thereto. The television camera 11c, being a stereo video camera similarly as the television camera 10c described above, comprises incidence lenses 11cL and 11cR (also referred to as television cameras 11cL and 11cR, in the following).

The objective lens 10a, the mirrors 3L and 3R, and the television cameras 11cL and 11cR are optically connected as described below. When reflected light from the operation site O transmits through the objective lens 10a, a portion of it (light flux FL2) is reflected by the mirror 3L and enters the television camera 11cL. Additionally, the other portion of the light transmitted through the objective lens 10a (light flux FR2) is reflected by the mirror 3R and enters the television camera 11cR.

In the television camera 11c, light fluxes FL2 and FR2 are converted into electric signals by a photoelectric converter (not shown), which the electric signals are transmitted to the image processor 5 through the signal line S1. Subsequently, the electric signals are transmitted to the small-size LCD 6 (6L and 6R) through the signal line S2 from the image processor 5, whereby images based on the light fluxes FL2 and FR2 are displayed by the stereo viewer 21.

Next, the major effect brought about by the surgical microscope system 200 will be described, referring to FIGS. 5, 7, and 8. Here, similarly as the first embodiment, it is assumed that there is a figure in the operation site O, consisting of intersecting arrow and line segment with a circle located at one end of the line segment.

Figure 7:
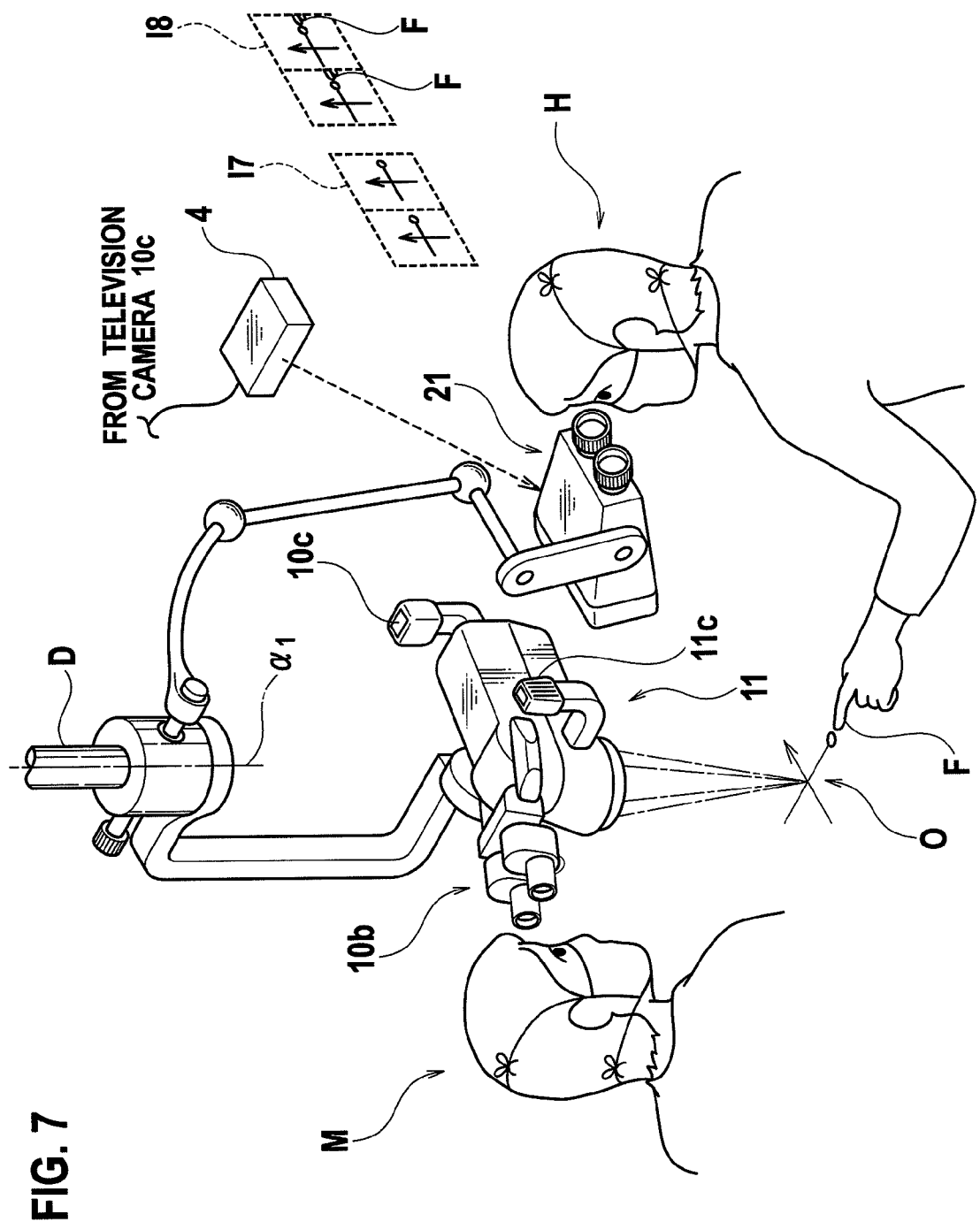
FIG. 7 is a perspective view illustrating the surgical microscope system according to the second embodiment of the present invention, presenting a comparative example to explain the effect of the stereo viewer.

As stated above, while the stereo viewer 21 receives the electric signals from the image processor 5 (FIG. 6) and displays the images based on light fluxes FL2 and FR2, it is assumed, as shown in the dotted arrow in FIG. 7, to receive the electric signals from the image processor 4 in the first embodiment and display the images based on the light fluxes FL and FR. In this case, as is apparent from the description in the first embodiment, the image provided by the stereo viewer 21 is identical to the image provided by the main microscope 11. In other words, the assistant operator H using the stereo viewer 21 sees the operation site O seen from the principal operator M using the main microscope 11. That is, as shown in FIG. 7, the assistant operator H sees, through the stereo viewer 21, a figure including an upward arrow and a circle located at the right side (I7). In this occasion, when the assistant operator H extends his/her finger F toward the operation site O, the finger F on the image comes out from the right side (I8). Therefore the assistant operator H can not properly grasp the sense of distance, thereby preventing proper assistance.

Figure 8:
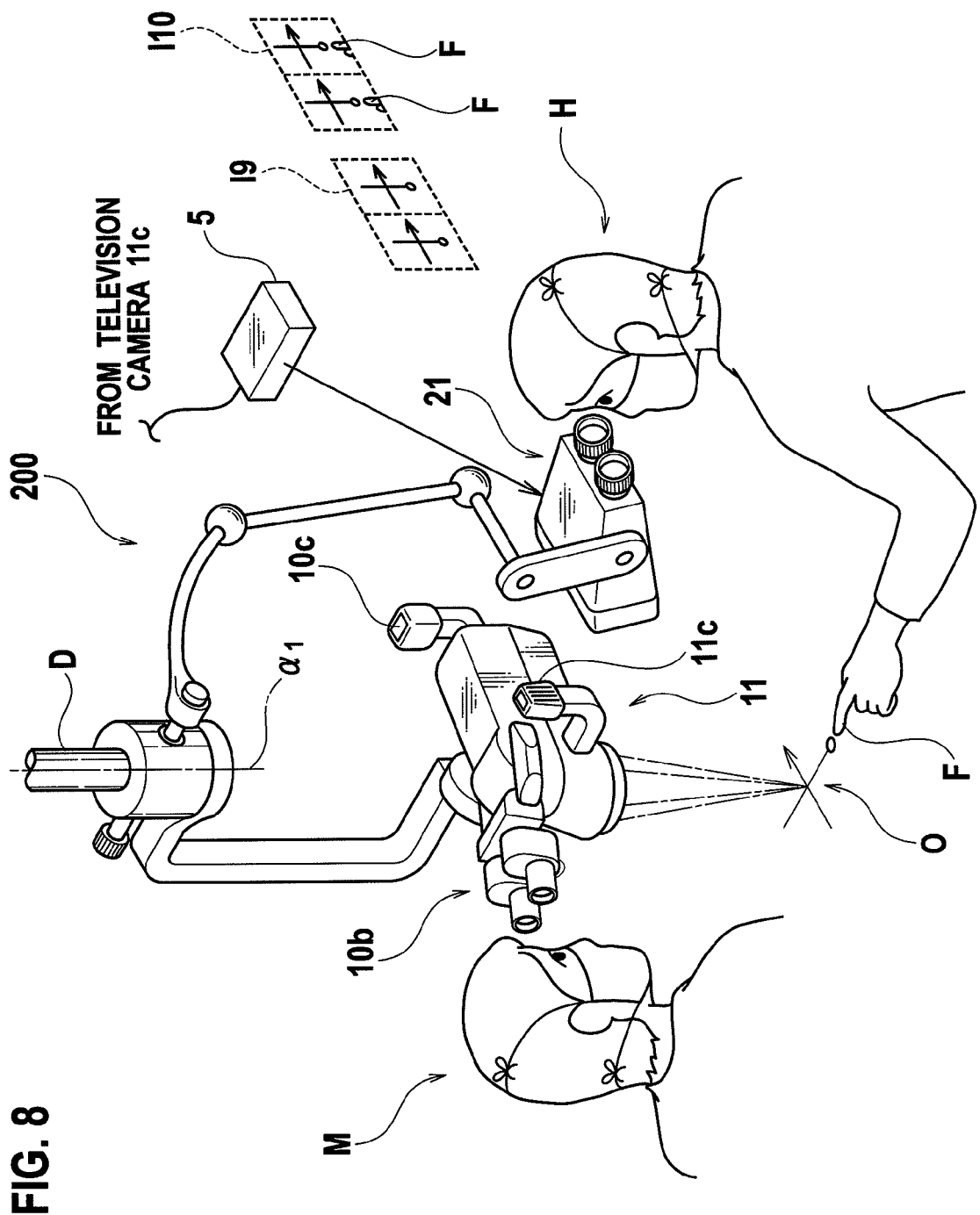
FIG. 8 is a perspective view illustrating the surgical microscope system according to the second embodiment of the present invention, in order to describe the effect of the stereo viewer in comparison with FIG. 7.

However, in reality, the stereo viewer 21 of the second embodiment receives the electric signals from the image processor 5 and displays the images based on the light fluxes FL2 and FR2 (FIG. 6), as shown in FIG. 8. Now focusing on the positional relationship between the light fluxes FL2 and FR2 defined by the mirrors 3L and 3R, and the light fluxes FL and FR defined by the beam splitters 1L and 1R, an imaginary line connecting the light fluxes FL2 and FR2, and an imaginary line connecting the light fluxes FL and FR are perpendicular to each other on the optical axis A. Since this positional relationship approximately reflects the positional relationship between the line of sight of the principal operator M and the line of sight of the assistant operator H, the principal operator M observes an image (images based on light fluxes FL and FR) corresponding to the operation site O observed by the position of the principal operator M through the ocular lens 10b of the main microscope 11, and the assistant operator H can observe an image (images based on light fluxes FL2 and FR2) corresponding to the operation site O observed by the position of the assistant operator H through the stereo viewer 21. In other words, according to the stereo viewer 21 in the second embodiment, the assistant operator H sees a figure consisting of a rightward arrow with a circle located at the bottom (I9 of FIG. 8). It is a magnified image of the operation site O observed by the assistant operator H from his/her position, whereby the assistant operator H sees his/her finger F coming out from below when the assistant operator H extends his/her finger F toward the operation site O (I10). Since the direction of the finger F being moved by the assistant operator H matches the direction of movement of the finger F seen through the stereo viewer 21, the assistant operator H can properly assist the surgery without losing sense of direction.

Here, it should be noted that the above-mentioned effects can not be brought about without the mirrors 3L and 3R, and the television camera 11c. Superficially, it may seem that an image of the operation site O seen from the position of the assistant operator H can be generated by suitably processing the image captured by the television camera 10c in the image processor 4 (FIG. 2). In this case, however, a stereoscopic image cannot be obtained. The reason for this will be described below, referring to FIGS. 9 and 10(a) to 10(c).

Figure 9:
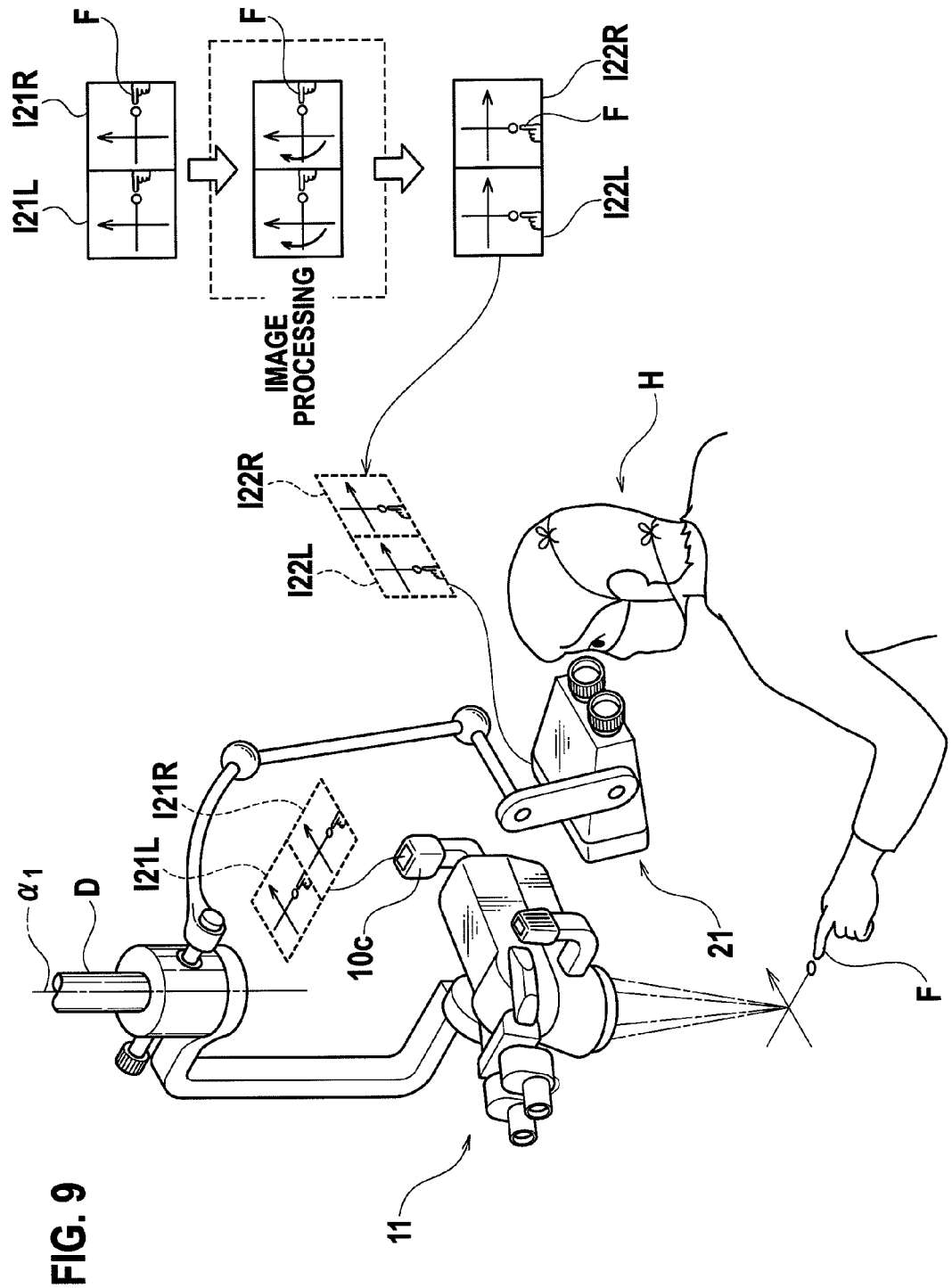
FIG. 9 is a schematic view illustrating a comparative example for describing the effect brought about by the surgical microscope system according to the second embodiment of the present invention.

In FIG. 9, images of the operation site O captured by the television camera 10c (10cL and 10cR) attached to the main microscope 11 are shown with reference numerals I21L and I21R. Since the television camera 10c provides images of the operation site O to be observed by the principal operator using the main microscope 11, as in the above description, the television camera 10c has captured a figure including an upward arrow and a circle located at the right side seen from the operator, and a finger F of the assistant operator H extending toward the circle. Here, it is assumed that the image I21L is rotated clockwise by 90° by image processing to obtain an image I22L, and the image I21R is rotated clockwise by 90° by image processing to obtain an image I22R. It is considered that a magnified image of the operation site O observed by the assistant operator H from his/her position can be provided, by displaying these images I22L and I22R by the stereo viewer 21.

However, a stereoscopic image cannot be provided by the images I22L and I22R. The reason will be explained, referring to FIGS. 10(a) to 10(c). Light from the focal point e of the objective lens 10a transmits through a point a of the objective lens 10a and arrives at the television camera 10c as the light flux FL, thereby forming the image I21L (FIG. 9). Additionally, light from the focal point e transmits through a point b of the objective lens 10a and arrives at the television camera 10c as the light flux FR, thereby forming the image I21R (FIG. 9). Now, since the light from the focal point e is refracted when transmitting through the objective lens 10a, the light flux FL is a light flux which has passed through a path ae that forms a predefined angle with a line segment af which is the extended line of the light flux FL. Similarly, the light flux FR is a light flux which has passed through not a line segment bg but a path be that forms a predefined angle with the line segment bg. Due to occurrence of such angle difference in the direction of alignment of the television cameras 10cL and 10cR, a stereoscopic image of an object located at the focal point e is formed.

Figure 10:
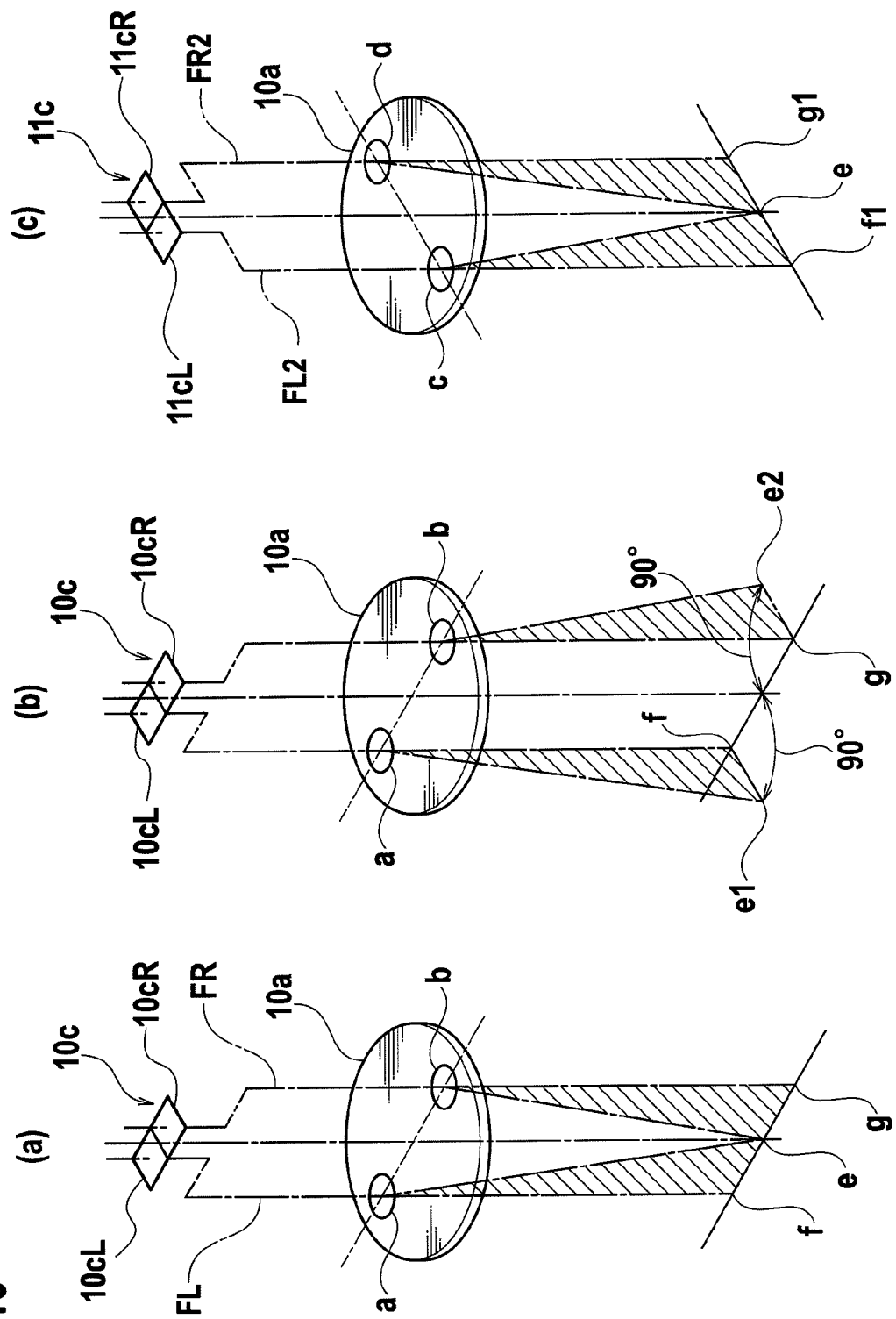
FIG. 10 is an explanatory drawing, to be referred together with FIG. 9, in order to describe the effect brought about by the surgical microscope system according to the second embodiment of the present invention.

Rotating the image based on the light flux FL described referring to FIG. 9 by 90° is equivalent with an image based on the light flux passed via a path ae1 resulted from rotating the path ae about a line segment af by 90° as shown in FIG. 10(b), while rotating the image based on the light flux FR by 90° is equivalent with an image based on the light flux passed via a path be2 resulted from rotating the path be about a line segment bg by 90°. Then, difference of angle which had been established between the light flux FL and the light flux FR along the direction of alignment of television cameras 10cL and 10cR no longer holds. Therefore, a stereoscopic image of an object located at the focal point e cannot be obtained.

Referring to FIG. 10(c), on the other hand, since the angle difference between the path from the focal point e to a point c on the objective lens and the line segment cf1, and the angle difference between the path from the focal point e to a point d on the objective lens and the line segment dg1 occur along the direction of alignment of the television cameras 11cL and 11cR, the television camera 11c can generate a stereoscopic image of an object located on the focal point e.

As has been described above, a stereoscopic image of the operation site O is displayed by the stereo viewer 21 using the mirrors 3 attached to the main microscope 11 and the television camera 11c, which is a further advantage that the surgical microscope system 200 according to the second embodiment has.

Third Embodiment

A surgical microscope system according to a third embodiment is identical to the surgical microscope system 200 of the second embodiment in terms of arrangement. However, the surgical microscope system according to the third embodiment differs from the surgical microscope system 200 in that the stereo viewer 21 is disposed so that the assistant operator H using the stereo viewer 21 can be positioned at the left-front of the principal operator M using the main microscope 11 and can face the operation site O from there.

Such an arrangement is realized by moving the stereo viewer 21 in the following manner, using the support member including the arms 31 to 34, the stereo viewer 21 being disposed at the right-front seen from the principal operator M using the main microscope 11 in the surgical microscope system 200.

Figure 11:
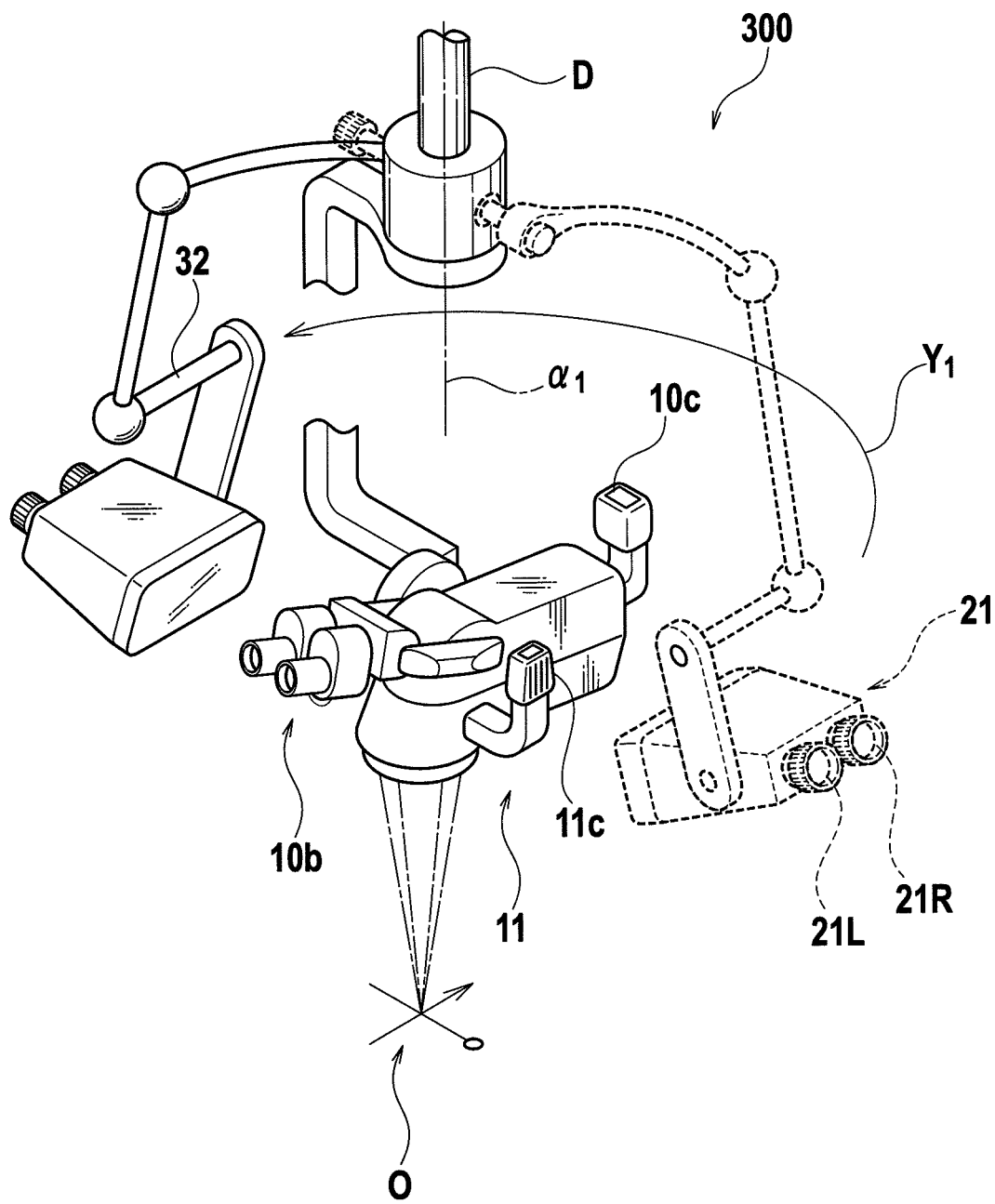
FIG. 11 is a perspective view describing the arrangement of a surgical microscope system according to a third embodiment of the present invention.
Figure 12:
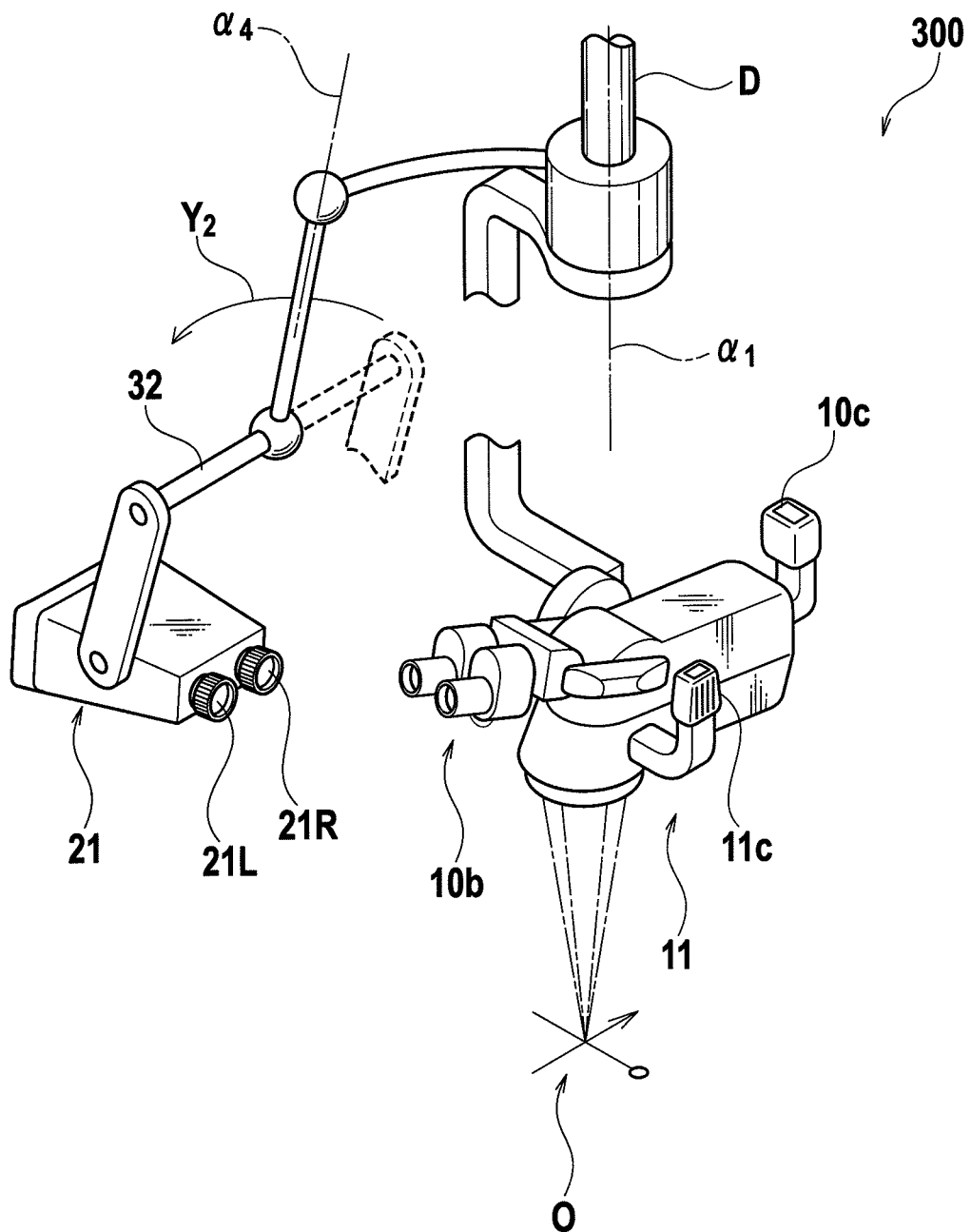
FIG. 12 is a perspective view describing, in conjunction with FIG. 11, the arrangement of a surgical microscope system according to the third embodiment of the present invention.
Figure 13:
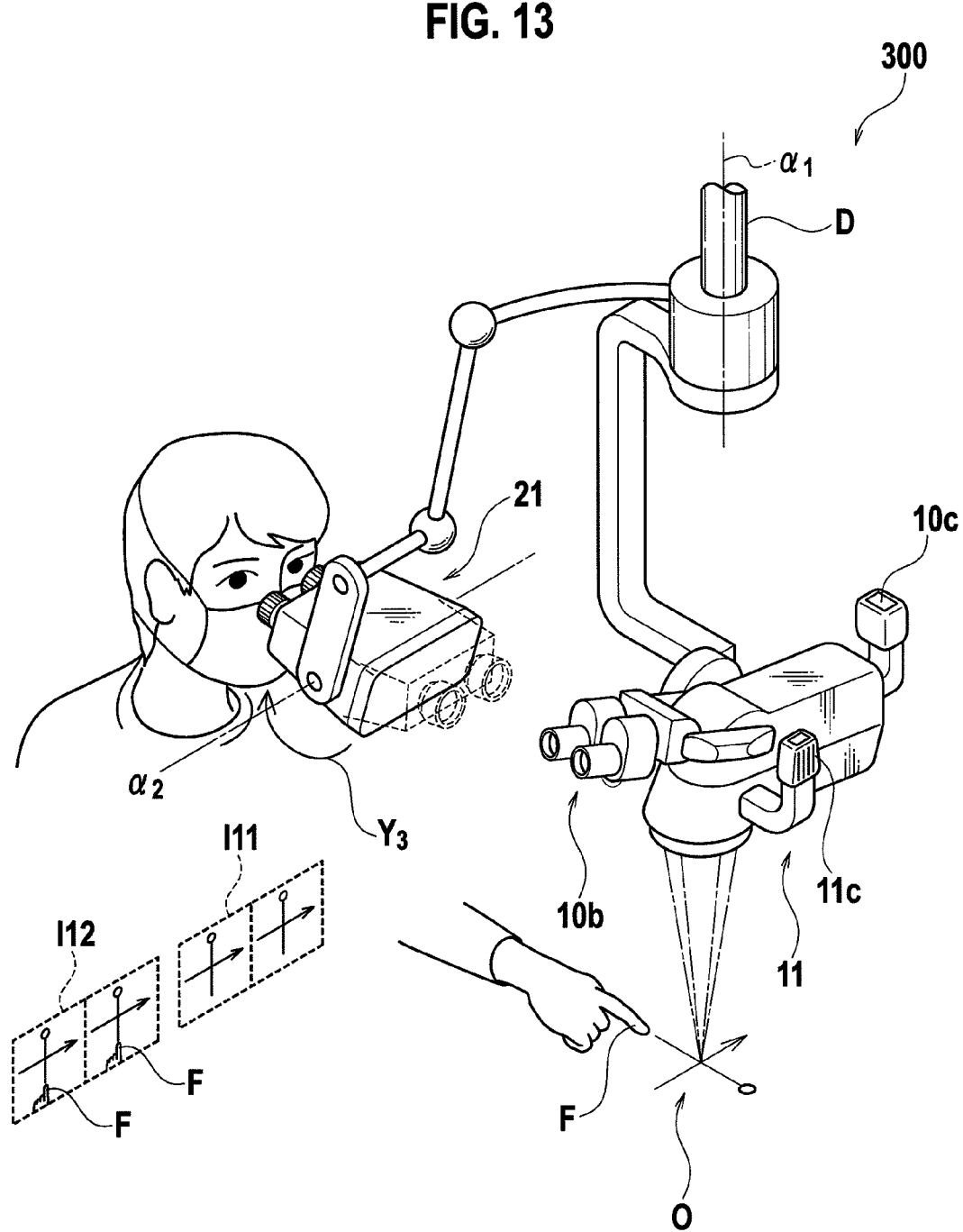
FIG. 13 is a perspective view describing, in conjunction with FIGS. 11 and 12, the arrangement of a surgical microscope system according to the third embodiment of the present invention.

Referring to FIG. 11, in the surgical microscope system 300 according to the third embodiment, the stereo viewer 21 is rotated about the axis $\alpha_1$ horizontally (arrow $Y_1$), and moved from the position of the stereo viewer 21 in the second embodiment (right-front of the main microscope 11) to a position opposite thereto (left-front of the main microscope 11). Next, as shown by the arrow $Y_2$ of FIG. 12, the arm 32 is rotated about the axis $\alpha_4$ (arrow $Y_2$), changing the orientation of the stereo viewer 21. In this occasion, the finders 21L and 21R of the stereo viewer 21 face the operation site O. Subsequently, as shown by the arrow Y3 of FIG. 13, the stereo viewer 21 is reversed about the axis $\alpha_2$.

By this reversal, the image displayed on the small-size LCD 6 (FIG. 6) within the stereo viewer 21 is also turned upside-down. As a result, the assistant operator H using the stereo viewer 21 sees a figure consisting of a leftward arrow with a circle located at the top (I11 of FIG. 13), and sees his/her finger F appearing from below (I12) when he/she extends his/her finger toward the operation site O. In other words, the surgical microscope system 300 according to the third embodiment is advantageous in that it allows the assistant operator H assists the surgery while seeing the operation site O which he/she is observing in a magnified manner from his/her position.

A further advantage of the surgical microscope system 300 according to the third embodiment is that the surgical microscope system 300 can be realized easily by using the surgical microscope system 200, without having to prepare a main microscope having a separate optical system.

Additionally, as stated above, the surgical microscope system according to the second or the third embodiment is advantageous in that two embodiments can be realized by suitably disposing the stereo viewer 21 at either the right-front or left-front of the main microscope 11.

Fourth Embodiment

Figure 14:
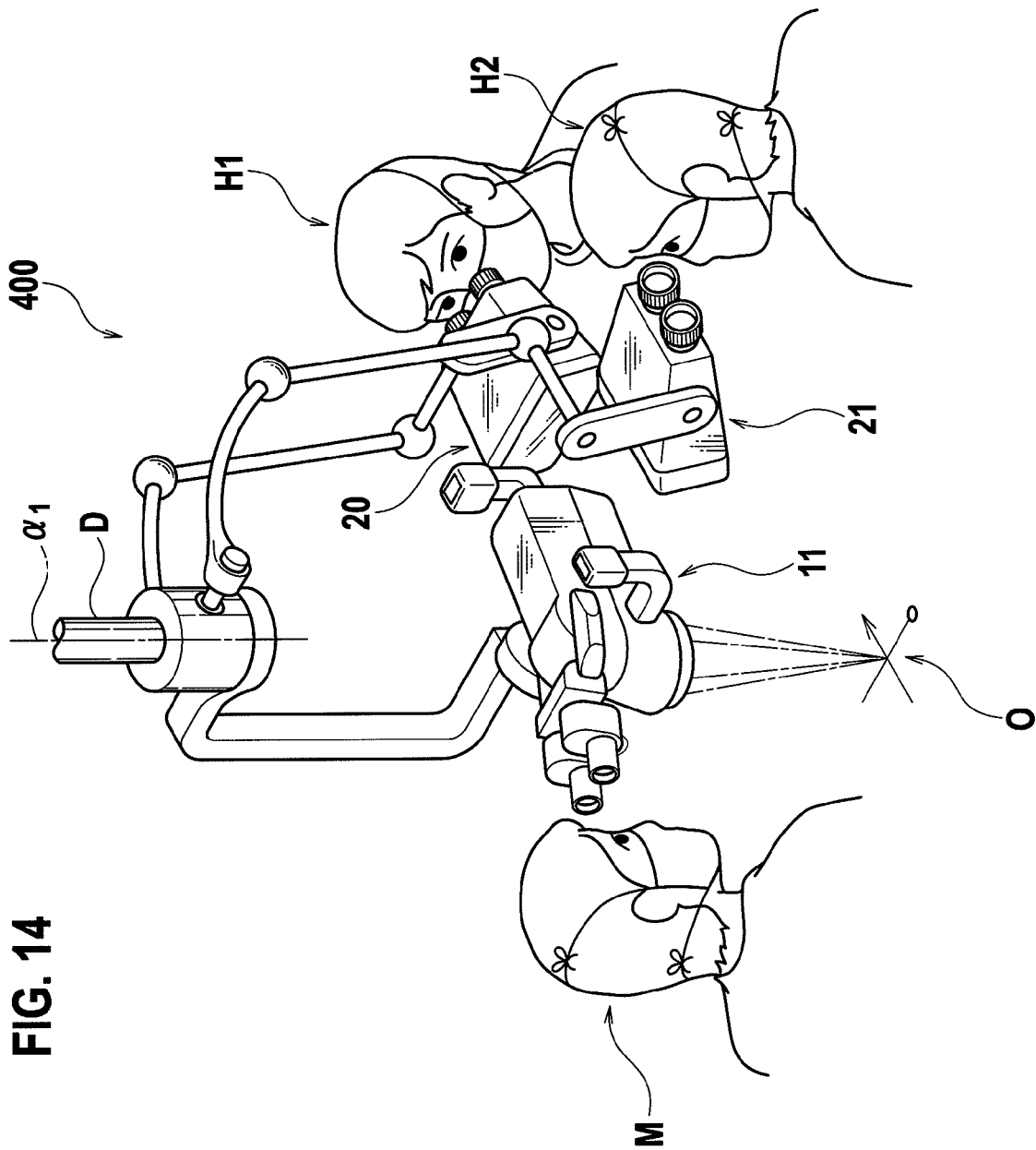
FIG. 14 is a perspective view illustrating a surgical microscope system according to a fourth embodiment of the present invention.

FIG. 14 is a schematic view illustrating a surgical microscope system according to a fourth embodiment. As shown, the surgical microscope system 400 according to the fourth embodiment comprises a main microscope 11, a stereo viewer 20, and a stereo viewer 21. The main microscope 11 has an arrangement identical to that of the second embodiment. That is, the main microscope 11 comprises an objective lens 10a, beam splitters 1L and 1R, ocular lenses 10bL and 10bR, mirrors 2L and 2R, and a television camera 10c (see FIG. 6). With the mirrors 2L, 2R and the television camera 10c, the stereo viewer 20 can display images which are identical to the images provided by the ocular lenses 10bL and 10bR of the main microscope 11. Furthermore, the main microscope 11 comprises mirrors 3L and 3R, and a television camera 11c (see FIG. 6). With the mirrors 3L, 3R and the television camera 11c, the stereo viewer 21 can display images corresponding to the operation site O observed by the assistant operator H2 from the right-front. In other words, the surgical microscope system 400 is arranged by adding the stereo viewer 20 in the first embodiment to the surgical microscope system 200 according to the second embodiment.

In addition, the main microscope 11, the stereo viewer 20, and the stereo viewer 21 are attached to the tip arm D of the medical optical instrument stand, respectively in an independently movable manner, by the arms already described in the first to third embodiments. In this case, it is needless to say that the stereo viewer 20 and the stereo viewer 21 are disposed so as not to block each other's movement.

With the above-mentioned arrangement, the surgical microscope system 400 according to the fourth embodiment is advantageous in that it allows microsurgery to be performed by three surgeons (M, H1, H2) using the main microscope 11, the stereo viewer 20, and the stereo viewer 21, respectively. Also, the surgical microscope system 400 has the effect and advantage of the stereo viewer 20 described in the first embodiment as it is. For example, it allows a first assistant operator H1 to assist the surgery while standing in alignment with or facing the principal operator M using the main microscope 11 (FIG. 14), and seeing the magnified image of the operation site observed from respective positions. Furthermore, the surgical microscope system 400 allows a second assistant operator H2 using the stereo viewer 21 to assist the surgery while standing at the right-front (FIG. 14) or left-front of the principal operator M using the main microscope 11, and seeing the magnified image of the operation site observed from respective positions.

Fifth Embodiment

Figure 15:
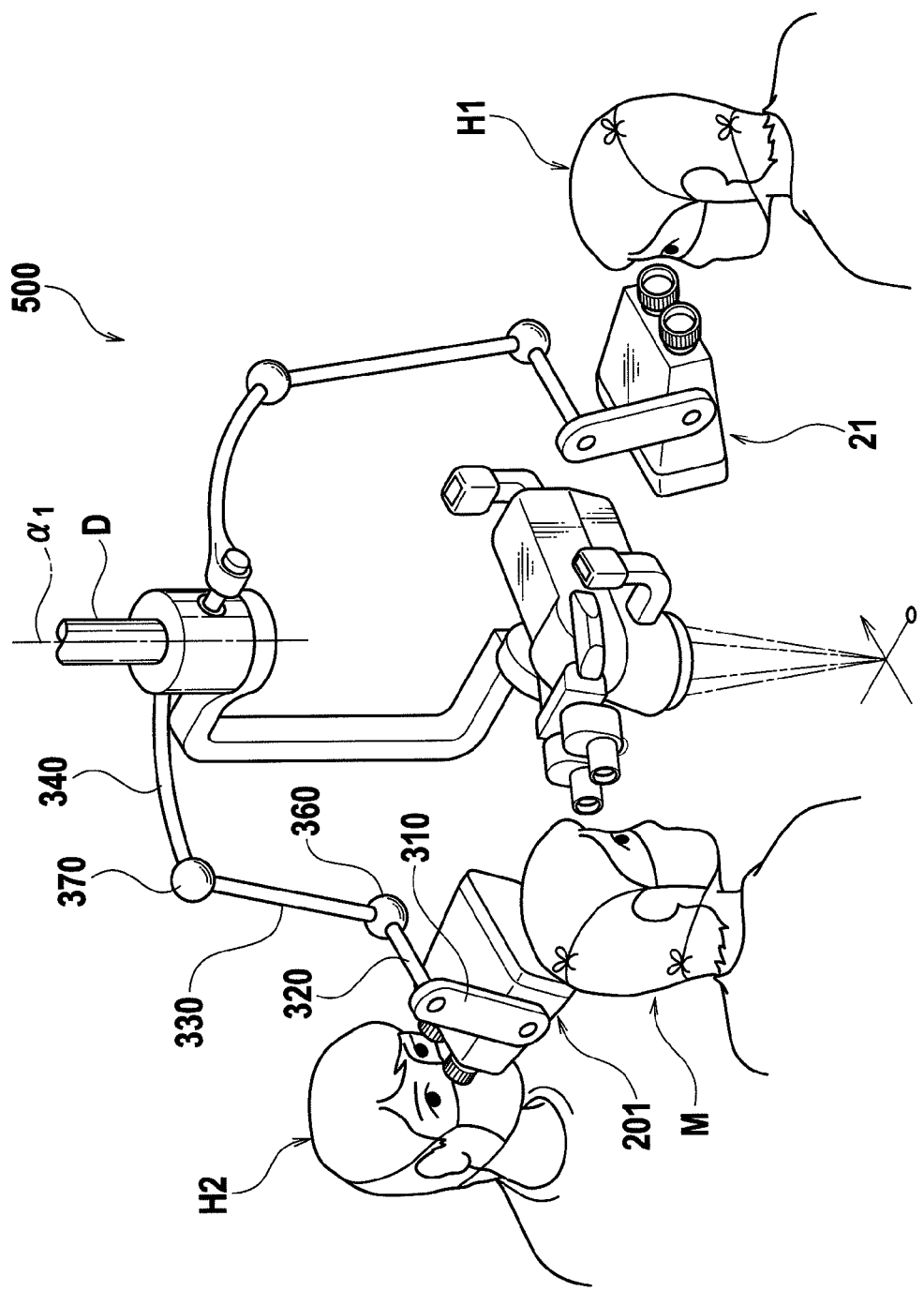
FIG. 15 is a perspective view illustrating a surgical microscope system according to a fifth embodiment of the present invention.

FIG. 15 is schematic view illustrating a surgical microscope system according to a fifth embodiment of the present invention. As shown, the surgical microscope system 500 according to the fifth embodiment comprises a main microscope 11, a stereo viewer 21, and a stereo viewer 201.

The main microscope 11 and the stereo viewer 21 have an arrangement identical to that of the second embodiment. In addition, the stereo viewer 21 is disposed so that the assistant operator H using it can be positioned at the right-front of the principal operator M using the main microscope 11 and can face the operation site O from there.

On the other hand, the stereo viewer 201 is attached to the tip arm D of the medical optical instrument stand by arms 310, 320, 330, 340 and joints 360, 370 so that it is disposed at a position opposite to the stereo viewer 21. In addition, although the stereo viewer 201 may have an arrangement identical to the stereo viewer 20, it does not have to be reversible and it is fixed to an arm 310 preliminarily reversed about the horizontal axis (needless to say, in terms of convenience of the assistant operator H2, it is desirable to be rotatable within a predefined angular range).

According to the above-mentioned arrangement, an image supposed to be displayed on the right-eye display surface of the stereo viewer 20 is turned upside down and provided to the left eye by the stereo viewer 201, whereas an image supposed to be displayed on the left-eye display surface of the stereo viewer 20 is turned upside down and provided to the right eye by the stereo viewer 201. Accordingly, with the stereo viewer 201, the assistant operator H2 can observe an image corresponding to the operation site O observed from a position opposite to the stereo viewer 21.

As thus described, with to the surgical microscope system 500 according to the fifth embodiment, two assistant operators H1 and H2 can assist the surgery while standing at the right-front and the left-front of the principal operator M using the main microscope 11, and seeing the magnified image of the operation site observed from respective positions. In addition, since a stereo viewer 201 can be obtained by separately preparing the stereo viewer 20 and suitably fixing it to the arm, microsurgery by three surgeons M, H1, H2 can be easily realized by simply supplying electric signals from the image processor without changing the optical structure inside the main microscope 11.

The surgical microscope system according to the present invention has been described in the above by presenting several embodiments. However, the present invention is not limited to them, and a variety of variations or modifications are possible.

It is needless to say that the optical structures of the main microscopes 10, 11 and the stereo viewers 20, 21 are not limited those mentioned above, and may be suitably constituted by adding predefined optical elements.

Although description has been provided in respective embodiments for a case where the main microscopes 10, 11 and the stereo viewers 20, 21, 201 are attached to the same medical optical instrument stand, they may be attached to separate stands if situation (space) of the operation room allows. In addition, the surgical microscope system according to the present invention may be arranged by suspending the main microscopes 10, 11 and the stereo viewers 20, 21, 210 from the ceiling of the operation, independently of each other.

Although, in the second or third embodiment, the optical system is arranged so that the main microscope 11 provides a stereoscopic image based on the light fluxes FL2 and FR2 defined by the mirrors 3L and 3R, and the stereo viewer 21 provides a stereoscopic image based on the light fluxes FL and FR defined by the beam splitters 1L and 1R, the arrangement of the optical system is not limited to this one. For example, the optical system may be arranged to guide an arbitrary light flux transmitted through the objective lens 10a to both of the ocular lenses 10bL and 10bR to provide a non-stereoscopic image by causing the ocular lenses 10bL and 10bR to provide identical images. In addition to this, the stereo viewer may be arranged to provide a non-stereoscopic image.

Although, in the fourth embodiment, the stereo viewer 20 is movably attached to the tip arm D by the supporting member including the arm 34, this is by no means limiting. It may be arranged such that the stereo viewer 20 is attached to the tip arm D using a predefined arm so that it is disposed in alignment with or opposite to the main microscope 11. It is also possible to arrange that the predefined arm is detachable to the tip arm D. In this manner, the stereo viewer 20 can be disposed in alignment with or opposite to the main microscope 11 if necessary, while the principal operator M and the assistant H1 are performing the surgery, with the stereo viewer 21 disposed suitably at the right-front or left-front of the principal operator M. On the contrary, it is apparent that the stereo viewer 20 can be movably attached and the stereo viewer 21 may be detachable.

Additionally, in the fourth embodiment, the stereo viewer 20 need not be reversible about the axis $\alpha_2$ when it is disposed at a position opposite to the main microscope 11. Apparently, it suffices to attach the stereo viewer, which is supposed to be disposed in alignment with the main microscope 11, to the arm 31 in a reversed manner so that it can be rotated about the axis $\alpha_2$.

In the fifth embodiment, it suffices that the stereo viewer 21 is rotatable about the axis $\alpha_1$ in a range which is sufficiently convenient for the assistant operator. This is because, in the fifth embodiment, it is not necessary to move the stereo viewer 21 to an opposite position since another stereo viewer 201 is disposed at the opposite position. The arm 340 may be detachable from the tip arm D.

Additionally, in the fifth embodiment, it is possible to detachably attach the arm 340 to the tip arm D, whereby the stereo viewer 201 can be detachable. In this manner, while the principal operator M and the assistant H1 are performing the surgery with the stereo viewer 21 suitably disposed at the right-front or left-front of the principal operator M, it is possible to attach the arm 340 to the tip arm D and dispose the stereo viewer 201 at a position opposite to the stereo viewer 21 when one more assistant becomes necessary.

Furthermore, in the fifth embodiment, although the main microscope 11 comprises the mirrors 2L, 2R and the television camera 10c similarly as the second embodiment, the mirrors 2L, 2R, and the television camera 10c may be excluded. Even with such exclusion, images can be provided to the stereo viewers 21 and 201 by the mirrors 3L, 3R and the television camera 11c, and because the surgical microscope system 500 does not have a stereo viewer equivalent with the stereo viewer 20, the mirrors 2L, 2R and the television camera 10c are not necessary.

In addition, although a case has been described where two stereo viewers are used, it is apparent from the above description that three stereo viewers can be used.

INDUSTRIAL APPLICABILITY

According to the present invention, a surgical microscope system is provided which allows an assistant operator to observe the operation site in a magnified manner within his/her own visual field from a position in alignment with, or opposite to, or the right-front or left-front of, the principal operator.

The invention claimed is:

1. A surgical microscope system, comprising:
   a binocular microscope that includes an objective lens, a right ocular lens which provides a first image based on a first light flux transmitted through the objective lens, and a left ocular lens which provides a second image based on a second light flux transmitted through the objective lens; and
   a display that is disposable opposite to and in alignment with the binocular microscope, includes a right-eye image display for displaying the first image and a left-eye image display for displaying the second image, and is reversible about a horizontal axis extending in a direction along which the right-eye image display and the left-eye image display are located in alignment,
   wherein the binocular microscope and the display are configured to display the first image and the second image while being disposed adjacent one another and viewable in a same direction, and configured to display the first image and the second image while being disposed along a first same axis and viewable in opposite directions, and
   wherein the binocular microscope and the display are configured to be independently rotatable about a second same axis with the display being rotatable about the second same axis independently of the binocular microscope.

2. The surgical microscope system according to claim 1, further comprising a first bifurcator and a second bifurcator that bifurcate the first light flux and the second light flux transmitted through the objective lens, wherein
   the first image is provided by the right ocular lens using one of first light fluxes bifurcated by the first bifurcator, and the first image is displayed on the right-eye image display based on an other one of the first light fluxes, and
   the second image is provided by the left ocular lens using one of second light fluxes bifurcated by the second bifurcator, and the second image is displayed on the left-eye image display based on an other one of the second light fluxes.

3. The surgical microscope system according to claim 2, wherein the display further comprises an image processor into which the other one of the first light fluxes bifurcated by the first bifurcator and the other one of the second light fluxes bifurcated by the second bifurcator are incident.

4. The surgical microscope system according to claim 1, further comprising a supporting stand, wherein the binocular microscope and the display are attached to the supporting stand so that the binocular microscope and the display are movable about the supporting stand independently of each other.

5. The surgical microscope system according to claim 4, wherein the binocular microscope is independently rotatable about at least three axes.

6. The surgical microscope system according to claim 5, wherein the three axes are perpendicular to each other.

7. The surgical microscope system according to claim 4, wherein the display is independently rotatable about at least three axes.

8. The surgical microscope system according to claim 7, wherein the display is independently rotatable about six axes.

9. The surgical microscope system according to claim 7, wherein at least two of the three axes are parallel.

10. The surgical microscope system according to claim 1, wherein an image displayed by the display is configured to be reversed at a same position with respect to the second same axis by rotating the display 180° about a vertical axis and by reversing the display about the horizontal axis.

* * * * *

UNITED STATES PATENT AND TRADEMARK OFFICE
CERTIFICATE OF CORRECTION

PATENT NO.        : 8,786,946 B2
APPLICATION NO.   : 12/306119
DATED             : July 22, 2014
INVENTOR(S)       : K. Nakamura Page 1 of 1

It is certified that error appears in the above-identified patent and that said Letters Patent is hereby corrected as shown below:

In the Specification

At column 5, line 66 of the printed patent, please change "$\alpha_1$" to --$\alpha_3$--.

At column 6, line 3 of the printed patent, please change "$\theta_4$" to --$\alpha_4$--.

Signed and Sealed this
Tenth Day of February, 2015

Michelle K. Lee
*Deputy Director of the United States Patent and Trademark Office*